(12) United States Patent
Russell et al.

(10) Patent No.: US 6,500,144 B1
(45) Date of Patent: Dec. 31, 2002

(54) STEERABLE CATHETER AND SELF-MOUNTING CENTER SUPPORT FOR USE WITH SAME

(75) Inventors: M. Ann Russell, Fremont, CA (US); Dennis Michael O'Brien, Oceanside, CA (US); Raymond S. Figueroa, Jr., Fremont, CA (US); Steven Morency, Sunnyvale, CA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 65 days.

(21) Appl. No.: 09/663,082

(22) Filed: Sep. 15, 2000

(51) Int. Cl.[7] ................. A61M 31/00; A61M 37/00
(52) U.S. Cl. ................. 604/95.01; 600/585
(58) Field of Search ............... 604/95.01; 600/585; 607/122, 101; 606/41

(56) References Cited

U.S. PATENT DOCUMENTS

| | | | | |
|---|---|---|---|---|
| 4,838,859 A | * | 6/1989 | Strassmann | 604/95 |
| 4,841,976 A | * | 6/1989 | Packard et al. | 128/657 |
| 4,934,340 A | * | 6/1990 | Ebling et al. | 128/6 |
| 5,308,324 A | * | 5/1994 | Hammerslag et al. | 604/95 |
| 5,603,697 A | * | 2/1997 | Grundy et al. | 604/95 |
| 5,628,775 A | * | 5/1997 | Jackson et al. | 607/116 |
| 5,676,653 A | * | 10/1997 | Taylor et al. | 604/95 |
| 5,702,433 A | * | 12/1997 | Taylor et al. | 607/101 |
| 5,728,144 A | * | 3/1998 | Edwards et al. | 607/101 |
| 5,843,031 A | * | 12/1998 | Hermann et al. | 604/95 |
| 5,857,997 A | * | 1/1999 | Cimino et al. | 604/95 |
| 5,871,525 A | * | 2/1999 | Edwards et al. | 607/104 |
| 5,904,667 A | * | 5/1999 | Falwell | 604/95 |
| 5,928,191 A | * | 7/1999 | Houser et al. | 604/95 |
| 5,944,689 A | * | 8/1999 | Houser et al. | 604/95 |
| 6,287,301 B1 | * | 9/2001 | Thompson et al. | 606/33 |

* cited by examiner

Primary Examiner—Denise L. Esquivel
Assistant Examiner—Marc Norman
(74) Attorney, Agent, or Firm—Henrick, Slavin & Holmes LLP

(57) ABSTRACT

A center support including a steering member and a mounting member integral with the steering member. The center support may be mounted on an internal support member within a catheter without the use of a ferrule.

33 Claims, 5 Drawing Sheets

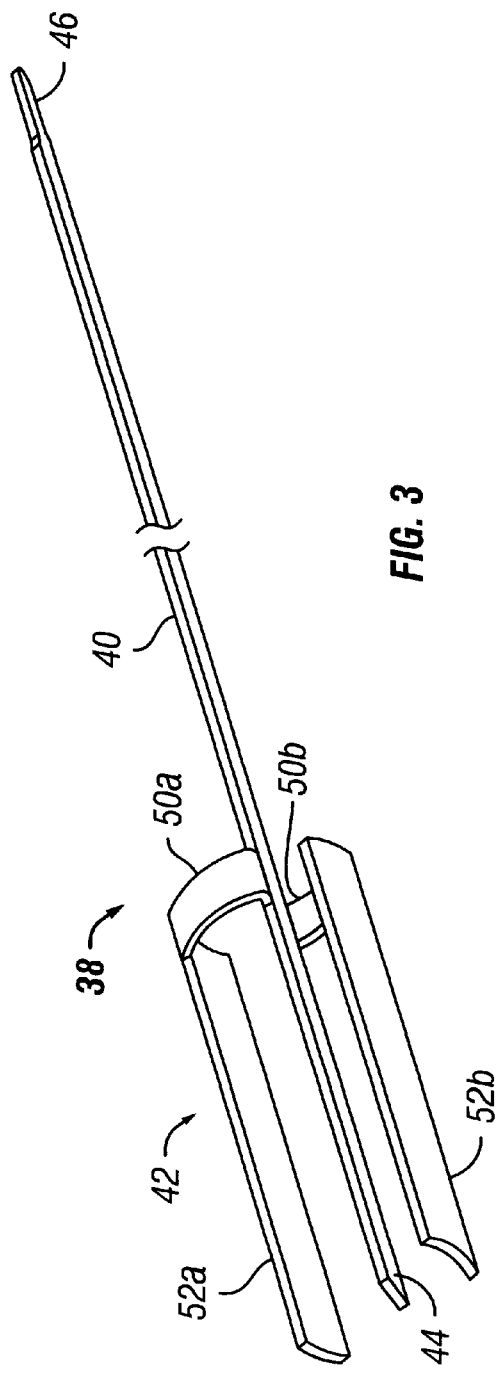
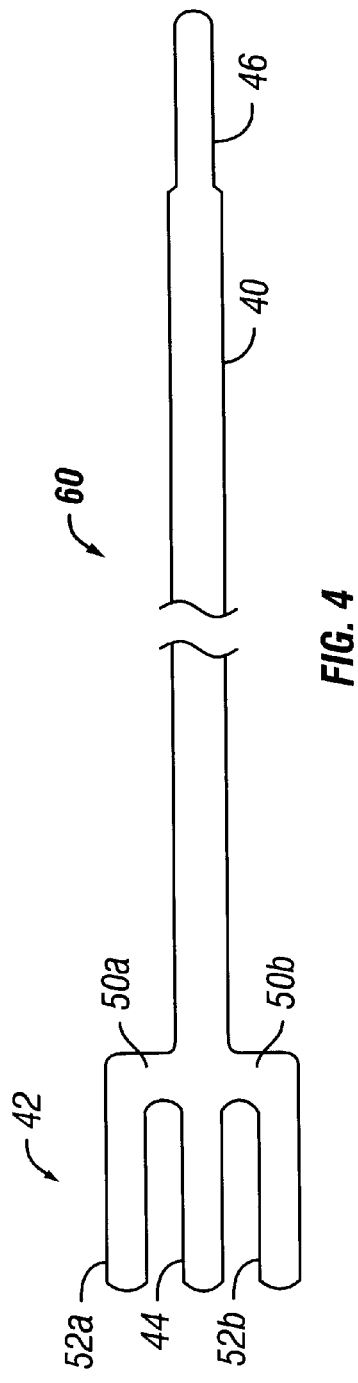

STEERABLE CATHETER AND SELF-MOUNTING CENTER SUPPORT FOR USE WITH SAME

BACKGROUND OF THE INVENTIONS

1. Field of the Inventions

The present inventions relate generally to catheters.

2. Description of the Related Art

Catheters, which are in widespread medical use today, allow physicians to gain access into interior regions of the body in a minimally invasive manner. Catheters are frequently used to advance electrodes, biopsy devices, and other operative elements through bodily lumens to an intended treatment site. In cardiac treatment, for example, the catheter is advanced through a main vein or artery into the region of the heart that is to be treated.

Although precise control of catheter movement is of paramount importance in all catheter-based procedures, the need for careful and precise control over the catheter is especially critical during certain procedures concerning the heart. These procedures, called electrophysiological therapy, are becoming more widespread for treating cardiac rhythm disturbances. Cardiac tissue coagulation (sometimes referred to as "ablation"), where therapeutic lesions are formed in cardiac tissue, is one procedure in which the ability to precisely position the distal end of the catheter is especially important. Incremental distal end movements of 1 mm to precisely position electrode(s) carried on or near the catheter tip are not uncommon and it can take up to an hour to precisely position the tip. In those instances where multiple electrode distal assemblies are employed, it is important that all of the electrodes achieve intimate tissue contact.

Some catheters are steerable in that the distal tip can be manipulated with a distal tip steering mechanism that is operably connected to the catheter handle by a steering control wire. The steering mechanism consists primarily of a center support (also referred to as a "steering spring"). The center support is mounted on the distal end of an elongate guide coil and extends to the distal tip of the catheter. The guide coil extends to the proximal end of the catheter. A ferrule, which is a cap-like device that may be positioned on the distal end of the guide coil, is used to mount the center support. The ferrule includes a slot for the center support and one or more openings through which the steering wires pass.

Steerable catheters also typically include a catheter body formed from two tubular parts, or members. The proximal member is relatively long and is attached to the handle, while the distal member, which is relatively short, carries the electrodes or other operative elements. In addition, the proximal member is typically formed from material, such as braided Pebax®, which has better torque transmission properties than the distal member, which is typically formed from a softer, more flexible material such as Pebax® that is better for steering.

In addition to steerability, torque transmission is important because physicians will often attempt to control the position of the distal end of the catheter by rotating the handle at the proximal end. The ability of the physician to precisely control the location of the distal end is directly related to the fidelity of the catheter's transmission of torsional forces exerted on the proximal end to the distal end. Torque is transmitted to the tip from the proximal member by way of the distal member. Torque is also transmitted to the tip from the guide coil by way of the center support. To that end, the ferrule prevents rotation of the center support relative to the guide coil so that torque transfer can take place.

The inventors herein have determined that conventional steerable catheters are susceptible to improvement. More specifically, the inventors herein have determined that the configuration of the distal tip steering mechanisms in conventional steerable catheters is unnecessarily costly. For example, the inventors herein have determined that the configuration of the steering center support in conventional steerable catheters necessitates the use of a ferrule to mount the center support within the catheter.

SUMMARY OF THE INVENTIONS

Accordingly, the general object of the present inventions is to provide a catheter that avoids, for practical purposes, the aforementioned problems. One object of the present inventions is to provide a steerable catheter that can be manufactured in a more economical manner than conventional steerable catheters. Another object of the present invention is to provide a steering center support that can be mounted within the catheter without the use of a ferrule.

In order to accomplish some of these and other objectives, a center support in accordance with one embodiment of a present invention includes a steering member and a mounting member integral with the steering member. Such a center support provides a number of advantages over conventional center supports. For example, the integral mounting member allows the present center support to be mounted directly onto a guide coil or other internal support member. As such, the present center support eliminates the need for the ferrules that were required to mount the center supports onto the guide coils in conventional catheters. The integral mounting member also allows the center support to be fixedly secured to the guide coil or other internal support member, which results in high fidelity torque transmission from the internal support member to the catheter tip.

The above described and many other features and attendant advantages of the present inventions will become apparent as the inventions become better understood by reference to the following detailed description when considered in conjunction with the accompanying drawings.

BRIEF DESCRIPTION OF THE DRAWINGS

Detailed description of preferred embodiments of the inventions will be made with reference to the accompanying drawings.

FIG. 3 is a perspective view of a steering center support in accordance with a preferred embodiment of a present invention.

FIG. 4 is a plan view of a center support blank that may be used to form the steering center support illustrated in FIG. 3.

DETAILED DESCRIPTION OF THE PREFERRED EMBODIMENTS

The following is a detailed description of the best presently known modes of carrying out the inventions. This description is not to be taken in a limiting sense, but is made merely for the purpose of illustrating the general principles of the inventions.

The detailed description of the preferred embodiments is organized as follows:

I. Introduction
II. Exemplary Catheters and Steering Center Supports
III. Electrodes, Temperature Sensing and Power Control The section titles and overall organization of the present detailed description are for the purpose of convenience only and are not intended to limit the present inventions.

I. Introduction

Catheters in accordance with the present inventions may be used within body lumens, chambers or cavities for diagnostic or therapeutic purposes in those instance where access to interior bodily regions is obtained through, for example, the vascular system or alimentary canal and without complex invasive surgical procedures. For example, the inventions herein have application in the diagnosis and treatment of arrhythmia conditions within the heart. Other applications include the diagnosis or treatment of intravascular ailments in association with, for example, angioplasty or atherectomy techniques. The inventions herein also have application in the diagnosis or treatment of ailments of the gastrointestinal tract, prostrate, brain, gall bladder, uterus, and other regions of the body.

With regard to the treatment of conditions within the heart, the present inventions are designed to produce intimate tissue contact with target substrates associated with various arrhythmias, namely atrial fibrillation, atrial flutter, and supraventricular tachycardia. A physician may use catheters in accordance with the present inventions to position diagnostic electrodes, soft tissue coagulation electrodes (also referred to as "ablation electrodes"), and/or other operative elements in contact with tissue.

II. Exemplary Catheters and Steering Center Supports

Figure 1:
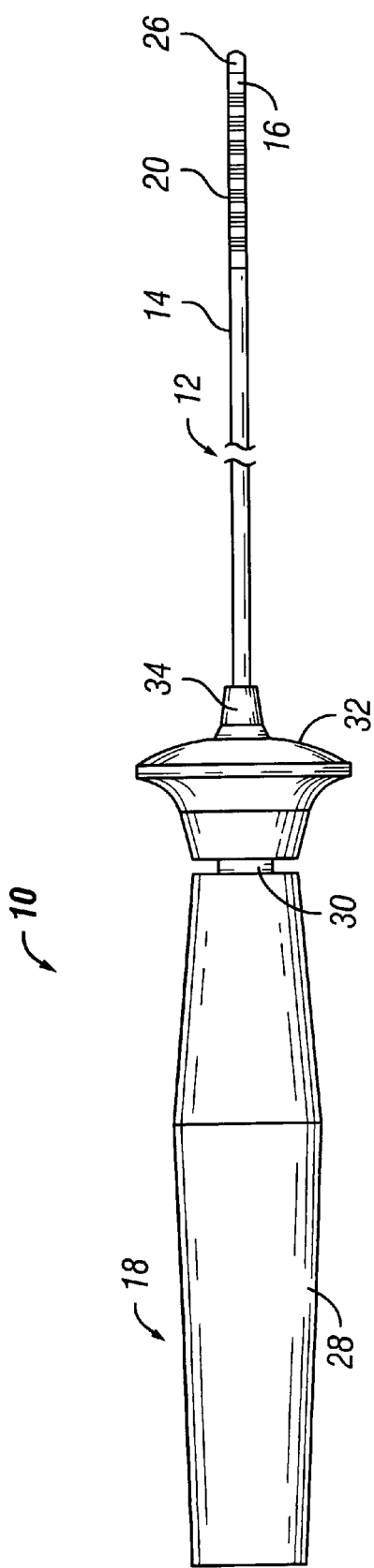
FIG. 1 is a side view of a catheter in accordance with a preferred embodiment of a present invention.
Figure 2:
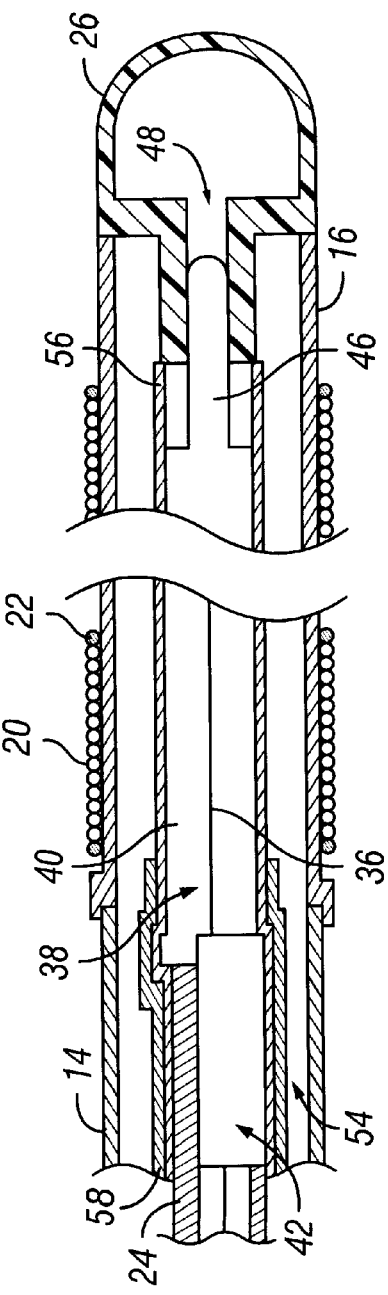
FIG. 2 is a side, partial section view of the distal portion of the catheter illustrated in FIG. 1.

A catheter 10 in accordance with a preferred embodiment of a present invention is illustrated in FIGS. 1 and 2. The illustrated embodiment includes a tubular catheter body 12 consisting of a proximal member 14 and a distal member 16. The proximal member 14 is relatively long and is attached to a handle 18, while the distal member 16, which is relatively short, carries a plurality of spaced electrodes 20 and/or other operative elements and temperature sensors 22. The proximal and distal members are preferably either bonded together with an overlapping thermal bond (as shown) or adhesive bonded together end to end over a sleeve in what is referred to as a "butt bond." The proximal member 14 is typically formed from a biocompatible thermoplastic material, such as a Pebax® material (polyether block emide) and stainless steel braid composite, which has good torque transmission properties. The distal member 16 is typically formed from a softer, more flexible biocompatible thermoplastic material such as unbraided Pebax® material, polyethylene, or polyurethane. An elongate guide coil 24 is provided within the proximal member 14 of the illustrated embodiment. Alternatively, a guide tube may be used. A tip electrode 26, or other tip member, may be fixedly mounted on the distal end of the distal member 16.

Although other handles may be employed, the exemplary handle 18 is a piston-type handle including a handle body 28, a piston 30, a thumb rest 32 and strain relief element 34. The exemplary catheter 10 also includes a steering wire 36 that is secured to a steering center support 38 by soldering or other conventional techniques. The proximal end of the steering wire 36 is secured within the handle 18. Thus, when the catheter body 12 is advanced in the distal direction by the piston 30, the steering wire 36 will pull on the center support 38, thereby causing the center support and distal member 16 to bend relative to the proximal member 14.

Additional details concerning piston-type handles are provided in U.S. Pat. No. 6,013,052, which is incorporated herein by reference. Catheters with piston-type handles typically include a single steering wire and are only steerable in one direction. For implementations of the present inventions that are steerable in more than one direction and include more than one steering wire, handles such as those disclosed in U.S. Pat. Nos. 5,531,686 and 5,820,591, which are also incorporated herein by reference, may be employed.

As illustrated for example in FIG. 3, the center support 38 preferably includes a steering member 40, to which the steering wire 36 is attached, and a mounting member 42 which mounts the center support onto the guide coil 24. A pair of tabs 44 and 46 are provided on the steering member 40. The proximal tab 44 is inserted into the guide coil 24. The distal tab 46 is inserted into a slot 48 on the tip electrode 26 and soldered, welded, chemical bonded or otherwise secured thereto. The exemplary mounting member 42 is integral with the steering member 40 and includes a pair of base members 50a and 50b as well as a pair of longitudinally extending engagement members 52a and 52b.

Figure 5:
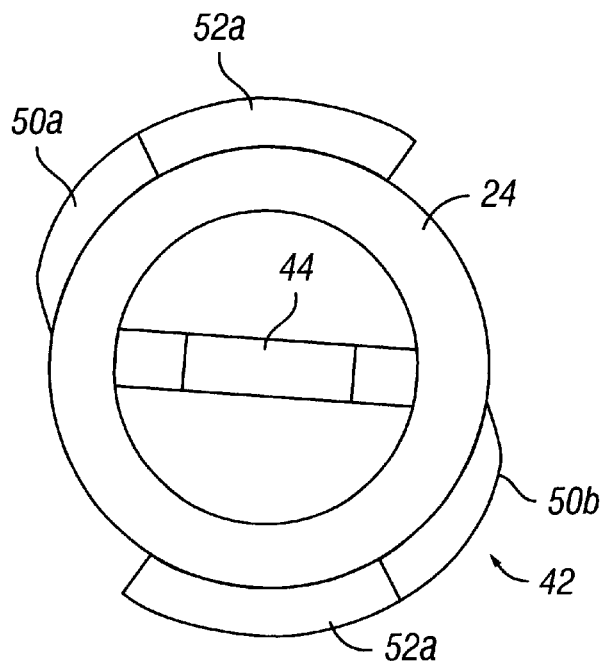
FIG. 5 is an end view of the steering center support and guide coil illustrated in FIG. 3.

The engagement members 52a and 52b have a curvature corresponding to that of the guide coil 24. In the illustrated implementation, the radius of curvature of the inner surfaces engagement members 52a and 52b closely corresponds to the outer radius of the guide coil 24. This allows the center support 38 to be mounted on the guide coil in the manner illustrated in FIGS. 2 and 5. Alternatively, the radius of curvature of the outer surface of the engagement members 52a and 52b will closely correspond to the inner radius of the guide coil 24. This allows the center support 38 to be mounted within the guide coil 24. Here, the proximal tab 44 may be eliminated. It should also be noted that guide coils may be non-cylindrical (i.e. non-circular in cross-section) and the engagement members 52a and 52b re-shaped in a manner that corresponds to the shape of the guide coil.

Regardless of the location (i.e. inside surface or outside surface of the guide coil) or configuration (i.e. circular or non-circular), the close fit provided by the mounting member 42 allows the center support 38 to be directly mounted onto the guide coil 24 and soldered, welded, chemical bonded or otherwise secured thereto. As such, the present center support 38 eliminates the need for the ferrules that were required to mount the center supports onto the guide coils in conventional catheters. Securing the center support directly to the guide coil also provides high fidelity torque transmission from the guide coil to the catheter tip.

A sleeve assembly 54 preferably covers the center support 38 and a portion of the guide coil 24. The exemplary sleeve assembly 54 is a two-part assembly including a Teflon sleeve 56 that is reinforced with Kevlar and a polyester tube 58. Of course, the sleeve assembly is not limited to the exemplary two-part assembly and other materials having similar properties may be used. The Teflon sleeve 56 is secured to the guide coil 24 and center support 38 by heat shrinking it thereover. The Teflon sleeve 56 is also treated with either sandpaper or sand blasting to make its outer surface rough, thereby preventing rotation of the various components relative to one another during the assembly process. Prior to heat shrinking the polyester tube 58 over the Teflon sleeve 56, adhesive material is inserted therebetween. Once the adhesive material sets and the heat shrink process is complete, a substantially unitary structure including the guide coil 24, tip electrode 26, center support 38 and sleeve assembly 54 will remain.

As illustrated for example in FIG. 4, the center support 38 may be formed from a flat blank 60. The blank 60 includes the structures that will ultimately make up the center support 38 and such structures are represented by the same reference numerals. Suitable metal materials for the blank include 304 stainless steel, beryllium copper and nickel titanium. The portion of the blank 60 corresponding to the mounting member 42 is bent through the use of a metal forming technique into the shape illustrated in FIGS. 2, 3 and 5. Alternatively, the center support 38 may be formed from a molded composite material.

The exemplary blank 60 illustrated FIG. 4 may be used to form a steering center support for a catheter that is utilized in the diagnosis and treatment of conditions within the heart. Such a blank is preferably formed from 304 stainless steel preferably with the following dimensions. [Length measurements are measured along the longitudinal axis of the center support and width measurements are perpendicular thereto.] The thickness of the blank is about 0.005 inch, which is constant from end to end, and the length is about 2.0 inches, but can be as long as 4.25 inches. The steering member 40 is about 1.7 inches long and about 0.035 inch wide. The tabs 44 and 46 are about 0.125 inch long and about 0.023 inch wide. Overall, the mounting member 42 is about 0.165 inch long and about 0.135 inch wide. The base members 50*a* and 50*b* are about 0.050 inch long, about 0.026 inch wide at their proximal ends and about 0.020 inch wide at their distal ends. The engagement members 52*a* and 52*b* are about 0.030 inch wide and the distance between the engagement members and the proximal tab 44 is about 0.026 inch. Of course, the dimensions are only exemplary and may be changed depending on the material used and/or the intended use of the center support.

Figure 6:
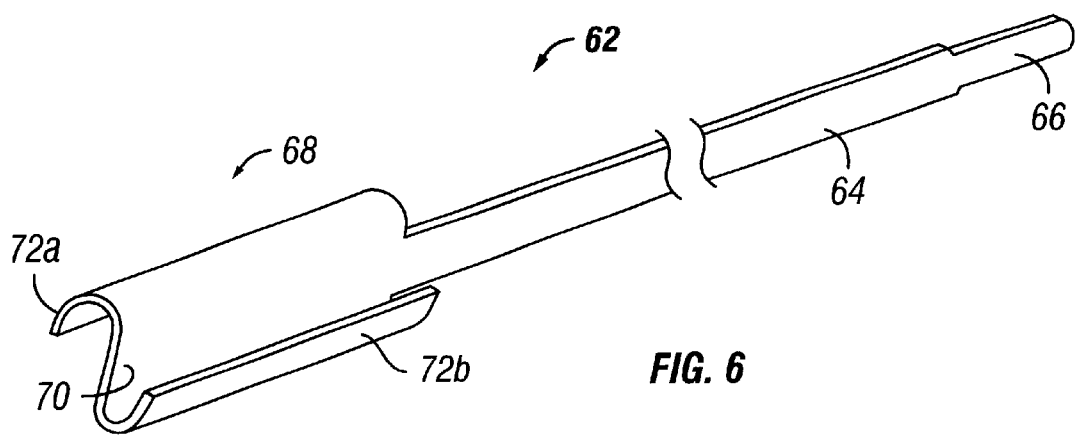
FIG. 6 is a perspective view of a steering center support in accordance with another preferred embodiment of a present invention.
Figure 7:
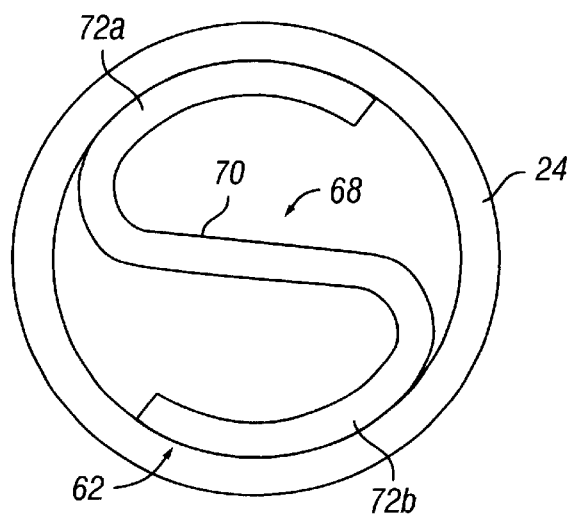
FIG. 7 is an end view of the steering center support illustrated in FIG. 6 mounted within a guide coil.

Another exemplary center support, which is generally represented by reference numeral 62, is illustrated in FIGS. 6 and 7. Center support 62 includes a steering member 64 and a distal tab 66. The center support also includes a mounting member 68 which is substantially S-shaped in cross-section along its entire length. As such, the mounting member 68 may only be positioned within the guide coil 24. The mounting member 68 includes a base member 70 and a pair of engagement members 72*a* and 72*b* which have a curvature corresponding to that of the guide coil 24. The curvature allows the engagement members 72*a* and 72*b* to be positioned adjacent to the inner surface of the guide coil 24 in the manner illustrated in FIG. 7. The engagement members 72*a* and 72*b* may then be soldered, welded, chemical bonded or otherwise secured to the guide coil 24 to secure the center support 62 in place.

Figure 8:
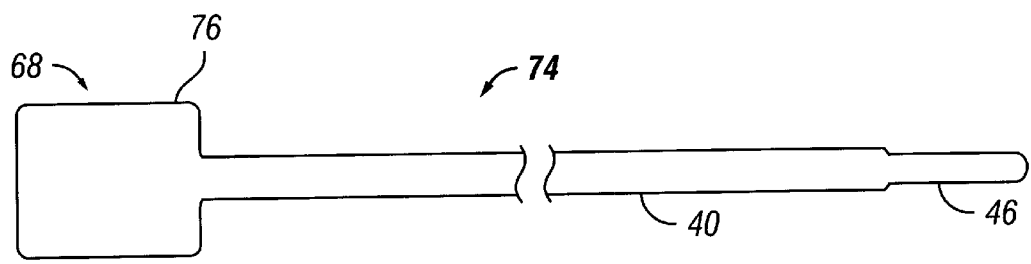
FIG. 8 is a plan view of a center support blank that may be used to form the steering center support illustrated in FIG. 6.

Turning to FIG. 8, the exemplary center support 62 may be formed from a flat blank 74 that is substantially similar to the blank illustrated in FIG. 4. Here, however, the base member 70 is formed from a rectangular element 76. The rectangular element 76 is preferably about 0.165 inch long and about 0.135 inch wide in those instances where the center support 62 is to be used in conjunction with a catheter that is utilized in the diagnosis and treatment of conditions within the heart. The flat blank 74 may be bent into the center support 62 by a suitable metal forming technique or molded from composite materials.

Figure 9:
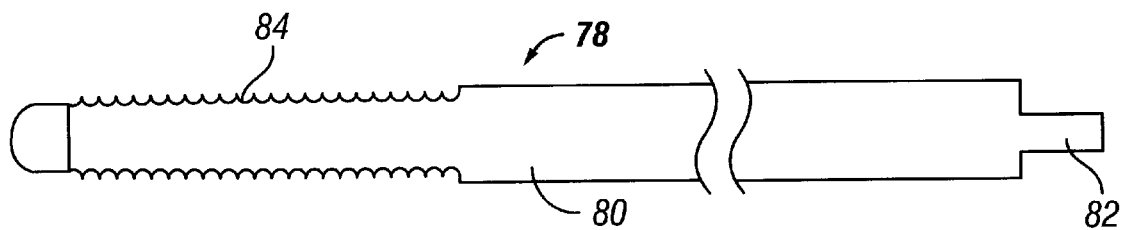
FIG. 9 is a plan view of a steering center support in accordance with still another preferred embodiment of a present invention.

Still another exemplary center support is illustrated in FIG. 9. Center support 78 includes a steering member 80 and a distal tab 82 substantially similar to those described above. Here, however, a flat mounting member 84 with threads formed in the side edges thereof that may be screwed into the guide coil 24 is provided. The threaded mounting member 84 may then be soldered, welded, chemical bonded or otherwise secured to guide coil 24 to secure the center support 78 in place. The pitch of the threads should be selected to correspond to that of the guide coil 24.

Figure 10:
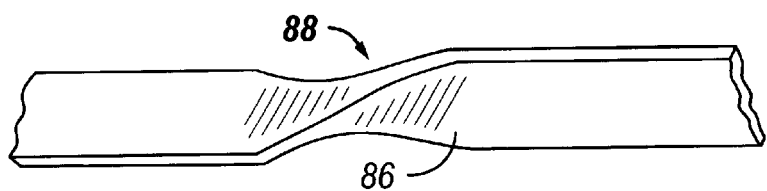
FIG. 10 is a side view of a portion of a steering center support in accordance with yet another preferred embodiment of a present invention.

The center supports illustrated in FIGS. 2, 6 and 9 will bend in a single bending plane. Nevertheless, center supports in accordance with the present inventions may also be configured such that they bend in more than one bending plane. Multi-plane bending may be accomplished by twisting the distal portion of a steering member relative to proximal portion. As illustrated for example in FIG. 10, a steering member 86, which may be substituted for the steering members in the center supports illustrated in FIGS. 2, 6 and 9, includes a 90 degree bend 88. Additional details concerning multi-plane bending may be found in U.S. Pat. No. 5,820,591.

The center supports illustrated in FIGS. 2, 6 and 9 may also be pre-bent in the direction opposite to the steering direction to provide two directional steering with a single steering wire.

III. Electrodes, Temperature Sensing and Power Control

In each of the preferred embodiments, the operative elements are a plurality of spaced electrodes 20. However, other operative elements, such as lumens for chemical ablation, laser arrays, ultrasonic transducers, microwave electrodes, and ohmically heated hot wires, and such devices may be substituted for the electrodes.

The spaced electrodes 20 are preferably in the form of wound, spiral coils. The coils are made of electrically conducting material, like copper alloy, platinum, or stainless steel, or compositions such as drawn-filled tubing (e.g. a copper core with a platinum jacket). The electrically conducting material of the coils can be further coated with platinum-iridium or gold to improve its conduction properties and biocompatibility. A preferred coil electrode is disclosed in U.S. Pat. No. 5,797,905. The electrodes 20 are electrically coupled to individual wires to conduct coagulating energy to them. The wires are passed in conventional fashion through a lumen extending through the associated catheter body into a PC board in the catheter handle, where they are electrically coupled to a connector that is received in a port on the handle. The connector plugs into a source of RF coagulation energy.

As an alternative, the electrodes may be in the form of solid rings of conductive material, like platinum, or can comprise a conductive material, like platinum-iridium or gold, coated upon the device using conventional coating techniques or an ion beam assisted deposition (IBAD) process. For better adherence, an undercoating of nickel or titanium can be applied. The electrodes can also be in the form of helical ribbons. The electrodes can also be formed with a conductive ink compound that is pad printed onto a non-conductive tubular body. A preferred conductive ink compound is a silver-based flexible adhesive conductive ink (polyurethane binder), however other metal-based adhesive conductive inks such as platinum-based, gold-based, copper-based, etc., may also be used to form electrodes. Such inks are more flexible than epoxy-based inks.

The flexible electrodes 20 are preferably about 4 mm to about 20 mm in length. In the preferred embodiment, the electrodes are 12.5 mm in length with 1 mm to 3 mm spacing, which will result in the creation of continuous lesion patterns in tissue when coagulation energy is applied simultaneously to adjacent electrodes. For rigid electrodes, the length of the each electrode can vary from about 2 mm to about 10 mm. Using multiple rigid electrodes longer than about 10 mm each adversely effects the overall flexibility of the device, while electrodes having lengths of less than about 2 mm do not consistently form the desired continuous lesion patterns.

The portion of the electrodes that are not intended to contact tissue (and be exposed to the blood pool) may be masked through a variety of techniques with a material that is preferably electrically and thermally insulating. This prevents the transmission of coagulation energy directly into the blood pool and directs the energy directly toward and into the tissue. For example, a layer of UV adhesive (or another adhesive) may be painted on preselected portions of the electrodes to insulate the portions of the electrodes not intended to contact tissue. Deposition techniques may also be implemented to position a conductive surface only on those portions of the assembly intended to contact tissue. Alternatively, a coating may be formed by dipping the electrodes in PTFE material.

The electrodes may be operated in a uni-polar mode, in which the soft tissue coagulation energy emitted by the electrodes is returned through an indifferent patch electrode (not shown) externally attached to the skin of the patient. Alternatively, the electrodes may be operated in a bi-polar mode, in which energy emitted by one or more electrodes is returned through other electrodes. The amount of power required to coagulate tissue ranges from 5 to 150 w.

A plurality of temperature sensors, such as thermocouples or thermistors, may be located on, under, abutting the longitudinal end edges of, or in between, the electrodes 20. Preferably, as illustrated for example in FIG. 2, temperature sensors 22 are located at the longitudinal edges of the electrodes 20. In some embodiments, a reference thermocouple may also be provided. For temperature control purposes, signals from the temperature sensors are transmitted to the source of coagulation energy by way of wires that are also connected to the aforementioned PC board in the catheter handle. Suitable temperature sensors and controllers which control power to electrodes based on a sensed temperature are disclosed in U.S. Pat. Nos. 5,456,682, 5,582, 609 and 5,755,715.

Finally, the electrodes 20 and temperature sensors 22 can include a porous material coating, which transmits coagulation energy through an electrified ionic medium. For example, as disclosed in U.S. Pat. No. 5,991,650, electrodes and temperature sensors may be coated with regenerated cellulose, hydrogel or plastic having electrically conductive components. With respect to regenerated cellulose, the coating acts as a mechanical barrier between the surgical device components, such as electrodes, preventing ingress of blood cells, infectious agents, such as viruses and bacteria, and large biological molecules such as proteins, while providing electrical contact to the human body. The regenerated cellulose coating also acts as a biocompatible barrier between the device components and the human body, whereby the components can now be made from materials that are somewhat toxic (such as silver or copper).

Although the present inventions have been described in terms of the preferred embodiment above, numerous modifications and/or additions to the above-described preferred embodiments would be readily apparent to one skilled in the art. By way of example, but not limitation, adhesive material can be introduced into the region of the catheter just proximal to the area where the proximal and distal catheter body members overlap to further improve torque transmission. The adhesive may be introduced though a small aperture in the catheter body. It is intended that the scope of the present inventions extends to all such modifications and/or additions.

We claim:

1. A center support for use in a catheter including an internal support member defining a distal end, the center support comprising:

a steering member defining a distal end and a proximal end; and a mounting member, integral with the steering member and located adjacent the proximal end of the steering member, adapted to mount the steering member onto the distal end of the internal support member.

2. A center support as claimed in claim 1, wherein the internal support member comprises a guide coil and the mounting member is adapted to mount the steering portion on the guide coil.

3. A center support as claimed in claim 1, wherein the internal support member comprises a cylindrical structure and the mounting member includes at least one curved surface adapted to engage the cylindrical structure.

4. A center support as claimed in claim 1, wherein the steering member includes a distal tab.

5. A center support for use in a catheter including an internal guide coil, the center support comprising:

a steering member defining a distal end and a proximal end; and a mounting member, integral with the steering member and located adjacent the proximal end of the steering member, including threads adapted to engage the guide coil and mount the steering member onto the guide coil.

6. A center support for use in a catheter including a cylindrical internal support member, the center support comprising:

a steering member defining a distal end and a proximal end; and a mounting member, integral with the steering member, located adjacent the proximal end of the steering member and including a pair of curved surfaces adapted to engage the cylindrical internal support member, adapted to mount the steering member onto the cylindrical internal support member.

7. A center support for use in a catheter including a cylindrical internal support member, the center support comprising:

a steering member defining a distal end and a proximal end; and a mounting member, integral with the steering member, located adjacent the proximal end of the steering member and including at least one curved surface adapted to engage the cylindrical internal support member, adapted to mount the steering member onto the cylindrical internal support member, at least a portion of the mounting member being substantially S-shaped in cross-section.

8. A center support as claimed in claim 7, wherein the entire mounting member is substantially S-shaped in cross-section.

9. A center support for use in a catheter including an internal support member, the center support comprising:
   a steering member defining a distal end and a proximal end; and
   a mounting member, integral with the steering member, located adjacent the proximal end of the steering member and including a pair of base members and a pair of longitudinally extending engagement members respectively associated with the base members, adapted to mount the steering member onto the internal support member.

10. A center support as claimed in claim 9, further comprising:
    a proximal tab located between the longitudinally extending engagement members.

11. A catheter center support blank, comprising:
    a steering member including a main portion defining a distal end, a proximal end and a steering member width; and
    a mounting member integral with the steering member, located adjacent to the proximal end of the steering portion, and defining a mounting member width substantially greater than the steering member width.

12. A catheter center support blank as claimed in claim 11, wherein the steering member and the mounting member are coplanar.

13. A catheter center support blank as claimed in claim 11, further comprising:
    a distal tab.

14. A catheter center support blank as claimed in claim 11, wherein the steering member includes a proximal tab.

15. A catheter center support blank as claimed in claim 11, wherein the mounting member comprises a pair of base members and a pair of longitudinally extending engagement members respectively associated with the base members.

16. A catheter center support blank as claimed in claim 15, wherein the steering member includes a proximal tab located between the longitudinally extending base members.

17. A catheter center support blank as claimed in claim 11, wherein the mounting member comprises a pair of substantially L-shaped members.

18. A catheter center support blank as claimed in claim 11, wherein the mounting member comprises a substantially rectangular member.

19. A catheter, comprising:
    a catheter body defining a distal end;
    an internal support member defining a distal end located within the catheter body such that the distal end of the internal support member is spaced from the distal end of the catheter body; and
    a center support including a steering member defining a distal end and a proximal end, and a mounting member, integral with the steering member and located adjacent to the proximal end of the steering member, mounted on the distal end of the internal support member.

20. A catheter as claimed in claim 19, wherein the internal support member comprises a guide coil.

21. A catheter as claimed in claim 19, wherein the internal support member comprises a cylindrical structure and the mounting member includes at least one curved surface adapted to engage the cylindrical structure.

22. A catheter as claimed in claim 19, wherein the catheter body includes a tip member and the steering member includes a distal tab fixedly secured to the tip member.

23. A catheter as claimed in claim 22, wherein the mounting member is fixedly secured to the internal support member.

24. A catheter as claimed in claim 19, wherein the mounting member is fixedly secured to the internal support member.

25. A catheter as claimed in claim 19, further comprising:
    at least one operative element carried by the catheter body.

26. A catheter as claimed in claim 19, wherein the catheter body comprises a proximal member defining a stiffness and a distal end and a distal member defining a stiffness that is less than the stiffness of the proximal member, and the internal support member comprises a tubular member that is located within the catheter body proximal member and defines a distal end that is substantially aligned with the distal end of the catheter body proximal member.

27. A catheter as claimed in claim 26, wherein the tubular member comprises a coil.

28. A catheter, comprising:
    a catheter body;
    an internal guide coil located within the catheter body; and
    a center support including a steering member defining a distal end and a proximal end, and a mounting member, integral with the steering member and located adjacent to the proximal end of the steering member, including threads adapted to engage the guide coil and mount the steering member onto the guide coil.

29. A catheter, comprising:
    a catheter body;
    a cylindrical internal support member located within the catheter body; and
    a center support including a steering member defining a distal end and a proximal end, and a mounting member, integral with the steering member, located adjacent to the proximal end of the steering member and including a pair of curved surfaces adapted to engage the cylindrical internal support member, adapted to mount the steering member onto the cylindrical internal support member.

30. A catheter, comprising:
    a catheter body;
    a cylindrical internal support member located within the catheter body; and
    a center support including a steering member defining a distal end and a proximal end, and a mounting member, integral with the steering member, located adjacent to the proximal end of the steering member and including at least one curved surface adapted to engage the cylindrical internal support member, adapted to mount the steering member onto the cylindrical internal support member, at least a portion of the mounting member being substantially S-shaped in cross-section.

31. A catheter as claimed in claim 30, wherein the entire mounting member is substantially S-shaped in cross-section.

32. A catheter, comprising:
    a catheter body;
    an internal support member located within the catheter body; and
    a center support including a steering member defining a distal end and a proximal end, and a mounting member, integral with the steering member, located adjacent to the proximal end of the steering member and including a pair of base members and a pair of longitudinally extending engagement members respectively associated with the base members, adapted to mount the steering member onto the internal support member.

33. A catheter as claimed in claim 32, further comprising:
    a proximal tab located between the longitudinally extending engagement members.

* * * * *